United States Patent [19]

Chambron

[11] 4,085,749
[45] Apr. 25, 1978

[54] METHOD AND APPARATUS FOR CONTROLLING THE MOVEMENT OF FLUID TO AND FROM A SYRINGE

[75] Inventor: Edmond Chambron, Paris, France

[73] Assignee: Compagnie Generale de Radiologie, Paris, France

[21] Appl. No.: 756,665

[22] Filed: Jan. 4, 1977

[30] Foreign Application Priority Data

Jan. 14, 1976 France .................. 76 00887

[51] Int. Cl.² ............................................. A61M 5/00
[52] U.S. Cl. ............................ 128/215; 128/DIG. 12; 128/276
[58] Field of Search ............... 128/215, 216, 224, 230, 128/234, 218 R, 218 G, 218 P, 218 PA, 272.1, 272.3, 273, 276, 214 R, DIG. 12

[56] References Cited

U.S. PATENT DOCUMENTS 3,605,745  9/1971  Hodosh ........................... 128/218 A
3,965,897  6/1976  Lundquist ........................ 128/218 G

FOREIGN PATENT DOCUMENTS 2,158,911  5/1973  Germany ........................ 128/218 G
540,227    3/1956  Italy ................................. 128/218 G Primary Examiner—John D. Yasko
Attorney, Agent, or Firm—Edwin E. Greigg

[57] ABSTRACT

A syringe for injecting fluid into a body or for removing body fluids is coupled to move together with the piston of a double acting hydraulic actuator having two chambers. For the purpose of aspirating fluid into the syringe, the second chamber of the actuator has within it a liquifiable gas which exerts a constant pressure on the piston. The expulsion of fluid from the syringe is accomplished by the admission of a hydraulic medium under pressure to the first chamber of the actuator. The apparatus also includes a calibrating mechanism which preselects a quantity of hydraulic medium proportional to the quantity of fluid to be expelled from the syringe.

12 Claims, 4 Drawing Figures

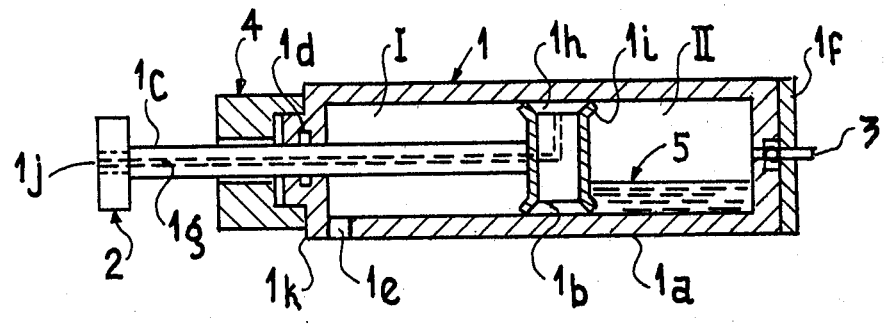
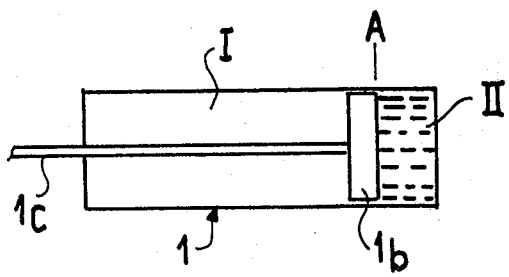
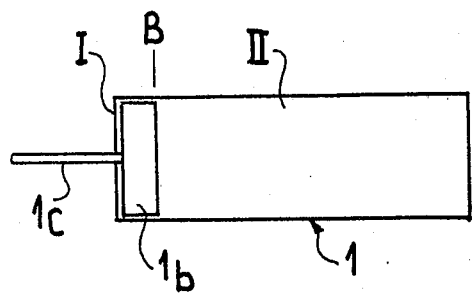

METHOD AND APPARATUS FOR CONTROLLING THE MOVEMENT OF FLUID TO AND FROM A SYRINGE

BACKGROUND OF THE INVENTION

The invention relates to a process and an apparatus for injection of a predetermined quantity of fluid into a body by means of a syringe operated by an actuating mechanism.

In many cases, the injection or withdrawal of fluids to and from tissue or blood vessels must take place at constant flow rate, i.e., independently of extraneous conditions such as the input resistance of the system, the viscosity of the fluid or the time limits imposed by the functioning of internal body organs.

Already known are syringes which are controlled by a single-action cylinder/piston actuator to which is admitted hydraulic pressure. The piston is returned by a spring, permitting refilling of the cylinder. However, the force exerted by this spring is proportional to its degree of compression and thus depends on the position of the piston. Because of the varying actuating pressure exerted on the piston, the known system cannot deliver a constant flow rate.

OBJECT AND SUMMARY OF THE INVENTION

It is an object of the present invention to provide a fluid injection mechanism which operates with a constant flow rate and thereby overcomes the disadvantages of the apparatus known in the state-of-the-art.

The invention further provides a process for injecting a volume of fluid into the vascular system of a body by means of a syringe which is controlled by a hydraulic actuator. The actuator includes at least one bicameral cylinder and a double-acting piston. According to the invention, the first chamber of the cylinder receives hydraulic fluid under pressure and with predetermined volume whereas the second chamber receives a liquifiable gas, the vapor pressure of which acts on the adjacent side of the piston and opposes the force of the hydraulic fluid. The liquifiable gas is one whose critical temperature is above the operating temperature and thus exhibits a saturated vapor pressure at the operating temperature.

Advantageously, the liquifiable gas introduced into the second chamber of the cylinder is taken from the family of chlorine and fluorine derivatives of methane and ethane, especially those whose saturated vapor pressure lies between 1.8 and 6 $kg/cm^2$ at 20° C.

Using the process of the invention, it becomes possible to provide a constant counterpressure in one of the chambers of the actuator without having to expend therefor external energy.

In a characteristic aspect of the invention, the amount of hydraulic fluid admitted under pressure to one of the chambers of the cylinder comes from a calibrated preselection cylinder and is then transferred to the first chamber of the actuator.

Furthermore, and independently of the preselection of hydraulic fluid under continuous pressure, the volume of liquid to be injected is aspirated by the expansion of the liquifiable gas at constant pressure within the second chamber of the actuator.

The invention further specifies an apparatus for carrying out the process of the invention and this apparatus includes an injection head for constant rate injection, including a control actuator for the syringe having at least a bicameral cylinder, the chambers being determined by the position of a sliding piston. The first chamber is subjected to hydraulic fluid under pressure and the second chamber is subjected to a counterpressure which is constant and which is generated by a liquifiable gas contained in the second chamber. The liquifiable gas is such that the critical temperature is above the normal operating temperature so that a saturated vapor pressure exists during normal operation. The apparatus of the invention further includes a mechanism for the preselection of hydraulic fluid volume which is introduced into the first chamber of the actuator under pressure. The two mechanisms are coupled by a flexible line.

In one embodiment of the invention, the preselector mechanism includes a cylinder with a piston which defines two chambers, the one being at high pressure and connected directly to a source of hydraulic fluid under pressure. The other chamber serves for the preselection of the volume of fluid and is connected to the source of fluid by some control means, for example an electromagnetic valve, and a flow controller connected in series between the preselection chamber and the first chamber of the actuator to permit transfer of the fluid from the preselection chamber to the first chamber of the actuator. The apparatus further includes means for causing the slow displacement of the piston and the actuator.

In another advantageous embodiment of the invention, the injection head has two parallel acting actuators each of whose pistons is connected mechanically by a common crossbar. A common input supplies each of the first chambers with hydraulic fluid under pressure and the piston of a syringe is connected to the crossbar.

The flexible hose connection between the two mechanisms should be non-conducting and the injection head is insulated electrically from the preselection mechanism.

The invention will be better understood and further objects and advantages thereof become more apparent from the ensuing detailed description of a preferred embodiment of the invention taken in conjunction with the drawing.

BRIEF DESCRIPTION OF THE DRAWING

FIG. 1 is a cross-sectional schematic view of an actuator for using the process of the invention;

FIG. 2 is an illustrative showing of one extreme position of the piston in FIG. 1;

FIG. 3 illustrates another extreme position of the piston in FIG. 1; and

DESCRIPTION OF THE PREFERRED EMBODIMENTS

Figure 4:
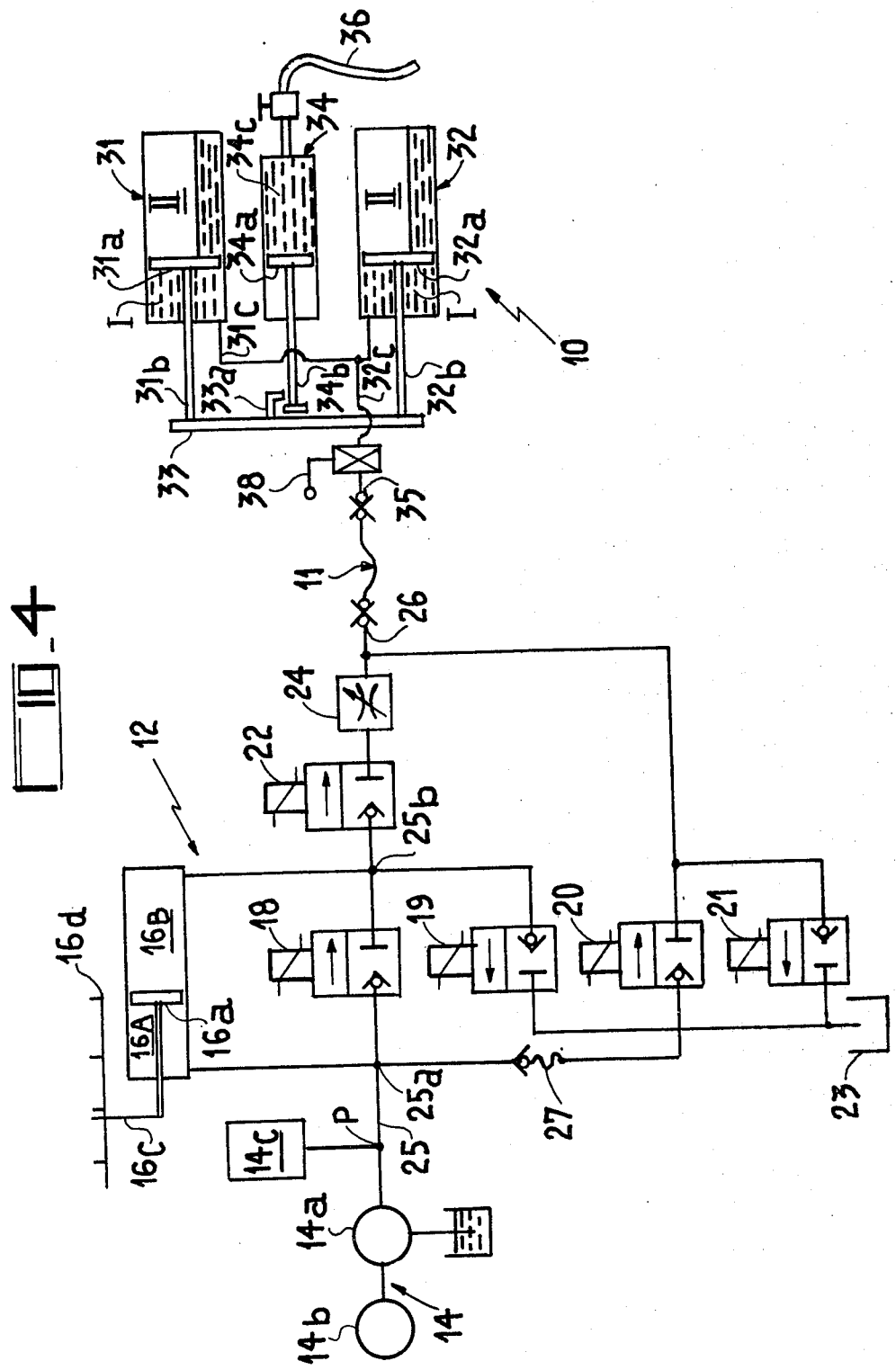
FIG. 4 is a schematic diagram for controlling the overall apparatus of the invention as well as showing an embodiment using two parallel actuators such as that in FIG. 1.

Turning now to FIG. 1, there is illustrated a section of an actuator 1 including a cylinder 1a and a piston 1b. A rod 1c, rigidly attached to the piston 1b, passes through a stuffing box 1d and is connected to a crossbar 2 which can also interact with the piston of an injection syringe (not shown).

A chamber I enclosing the piston rod 1c has an opening 1e for admitting pressurized hydraulic fluid, for example pressurized oil. A chamber II of the cylinder 1a has a charging valve 3 which can be reached from the outside through the base 1f.

An external channel 1g in the piston 1b and the piston rod 1c establishes communication between the space 1h lying between the piston elements 1i and a gas exit hole 1j which communicates with the outside of the rod 1c. This channel is provided so as to maintain the periphery of the piston 1b at atmospheric pressure so that the interior pressures urge the piston elements 1i against the internal walls of the cylinder 1a so as to maintain a reliable sealing action. Attached to an end face 1k of the cylinder is a guide block 4 which guides the motion of the piston 1b and which also determines its path so as to define the minimum volume of the chamber II. It is an established fact that, at temperatures below the critical temperature, the isothermal curves of a substance define a pressure level along which the substance exists in two phases, a liquid phase and a vapor phase. The pressure at this level is called the saturated vapor pressure.

By way of example, known liquifiable gases which have the appropriate qualities at ambient temperature are, for example, known commercially as "Freon" and "Forane" (12 or 14). These liquifiable gases belong to a class of refrigerants contained in the general group of chlorine and fluorine compounds of methane and ethane.

The substance "Forane" which is used by way of example, has a saturated vapor pressure lying between 1.8 and 6kg/cm$^2$ at a temperature of 20° C. The critical temperature of "Forane" is 112° C. In accordance with the method of the present invention, the chamber II (FIGS. 1-3) is filled with a liquifiable gas 5 which is introduced in the liquid phase through the valve 3.

In FIG. 2, the piston 1b is shown in a position A which corresponds to the minimum volume of the chamber 2 as determined by the guide block 4. In FIG. 3 the piston 1b is shown in its extreme position B defining the maximum volume of chamber II occupied by the gaseous phase of the liquifiable gas 5. The positions A and B correspond, respectively, to the extreme limits of the saturated vapor pressure within which still exist two phases at a temperature lying below the critical temperature of the substance. If hydraulic pressure is applied to chamber I, the piston 1b is displaced to the right in the figure in the cylinder 1a until the cross-bar 2 abuts the guide block 4 (position A) which defines the minimum volume of the chamber II and compresses the liquifiable gas at the pressure level defined above and forces it into the liquid phase. When the hydraulic pressure is removed, the liquified gas expands into its vapor phase which causes the piston to move toward the left in the figure at rigorously constant pressure into its position B (FIG. 3). In order to insure that the two phases be reversible, it is useful to permit a small fraction of saturated vapor to exist when the volume of chamber II is minimum (position A) and, on the other hand, to permit the existence of a few drops of liquified gas in the maximum volume of the chamber II (position B of the piston). The invention further provides an apparatus for injection of a fluid (FIG. 4) which permits the preselection of a specified volume of the fluid, for example a contrast material, and to provide for the reliable injection of that fluid into the vascular or muscular system of a person at a predetermined constant rate. For this purpose, the apparatus includes an injection head 10 designed for a constant flow rate and a preselection mechanism 12 connected thereto by a flexible coupling 11. The coupling may be made from any non-conducting material so as to provide electrical insulation of the injection head 10 from the mechanism 12. The mechanism 12 includes a source of hydraulic fluid 14, a preselection cylinder 16 and electromagnetic control valves 18 to 22. The hydraulic supply system 14 further comprises a pump 14a driven by a motor 14b as well as an accumulator 14c to maintain a given pressure P, for example 80 bars, at the junction 25a of the output conduit 25. On opposite sides of the piston 16a lie cylinder chambers 16A and 16B of a cylinder 16. The chamber 16A is connected directly to the channel 25 and the chamber 16B is connected via an electromagnetic valve 18 to the same channel 25. The chamber 16B may be emptied through the junction 25b into a tank 23 via an electromagnetic check valve 19. The tank 23 is open and is at atmospheric pressure.

The channel 25 is also connected to an output channel 26 via a calibrated check valve 27 and an electromagnetic valve 20 which controls the slow advance of the syringe 34. The slow return of the syringe is controlled by an electromagnetic valve 21 connected between the output channel 26 and the tank 23. An injection control valve 22 is connected in series with a flow regulator 24 between the junction 25b and the output channel 26. Due to these connections, the piston 16a assumes a position which corresponds to the difference between the forces exerted by the two fluids on the two opposite faces of the piston 16a. An indicator 16c cooperating with a scale 16d shows the amount of hydraulic fluid contained within the chamber 16B and this amount corresponds to the volume of fluid to be injected by the syringe 34. The injection head 10 also includes an actuator comprising two cylinders 31 and 32 substantially of identical construction, as well as a syringe 34. The piston rods 31b and 32b of pistons 31a and 32a, respectively, are joined by a common crossbar 33 which also includes means for attaching the rod 34b of piston 34a of the syringe 34.

According to the present invention, each of the cylinders 31 and 32 of FIG. 4 includes the chambers I and II previously illustrated in FIGS. 1-3. The chambers II are filled with a liquifiable gas from the class of gases recited above, while the chambers I contain a hydraulic fluid under pressure admitted through the input line 35 which feeds the channels 31c and 32c. The chamber 34c of the syringe is connected to a conduit 36 which may serve for the aspiration of the fluid to be injected or may be connected to the vascular system for the purpose of injection of the fluid contained in the syringe. The apparatus illustrated in FIG. 4 according to the invention functions as follows: In order to force the piston rods 31a and 31b from the cylinders 31 and 32, respectively, the chambers I are permitted to drain to the tank 23 by opening the electromagnetic valve 21 which permits an expansion of the liquifiable gas at constant pressure within the chambers II and the subsequent displacement of pistons 31a and 32a to the left as illustrated in FIG. 4. At the conclusion of this first operation, the syringe 34 on the injection head 10 may be put in place or exchanged. In order to cause the piston rods 31b and 32b to move into the respective cylinders so as to also drive the piston 34a into the syringe in the sense of forcing the evacuation of the syringe, one needs only to open the electromagnetic valve 20 and leave all the other valves closed. In that condition, hydraulic pressure from the channel 25 acts on the pistons 31a and 32a which are thereby displaced and compress the saturated vapor contained in the chambers II. During this displacement, the common crossbar 33 locks onto the rod 34b by means of the locking mechanism 33a. When the pistons 31a and 32a occupy a position corresponding to a minimum volume of the chambers II, the valve 20 is closed. As described above, the electromagnetic valve 21 controls the operation of aspiration of fluid into the syringe 34. In order to make a preselection of the volume of fluid to be injected, it is sufficient to move the piston 16a so as to place the indicator 16c at the chosen indication of the scale 16d. This movement is controlled by the electromagnetic valves 18 and 19, one of which applies the pressure P on one face of the piston 16a and the other diminishes the pressure on that same face. Subsequently, the valves 18 and 19 are closed, and the valves 22 and the regulator 24 are opened, so that the preselected volume is forced from the chambers 16 toward the conduit 26 under the action of the pressure P which is exerted in the chamber 16A on the piston 16a. Thus, the volume 16B is forced through the flexible coupling 11 and moves through the conduit 35 and the tubes 31c, 32c into the chambers I of the two cylinders 31 and 32. Inasmuch as the piston rods 31b and 32b of pistons 31a and 32a are rigidly attached to the crossbar 33 which controls the movement of the rod 34b of the piston 34a of the syringe, the displacement of these pistons results in a similar displacement of the piston 34a. As a consequence, when the chambers I have been filled with a predetermined volume 16b with hydraulic fluid under pressure, the pistons 31a and 32a are thereby displaced so as to also move the piston 34a in a direction and over a path which discharges a similar volume of liquid through the conduit 36. It will be understood that the chambers I of each of the cylinders 31 and 32 must receive a total volume which corresponds to the volume 16b and to that of the injection chamber 34c.

The discharge of the accumulator 14c may be prevented by electrical or mechanical mechanisms which inhibit the operation of the electromagnetic valves 18 and 19 and those of the valves 20 and 21. The control of the valves 18 to 22 may be made manually, pneumatically or electrically.

The speed of movement of the pistons 31a and 32a may also be changed at will by actuating a manual control valve 38 inserted in the input channel 35 of the injection head 10. One of the principal advantages of the present invention is that hydraulic fluid may be displaced under pressure by actuating the electromagnetic valves 20 and 21 which have a hydraulic circuit which is separated from that of the electromagnetic valves 18 and 19.

The foregoing relates to preferred embodiments of the invention, it being understood that other embodiments and variants are possible within the spirit and scope of the invention, the latter being defined by the appended claims.

What is claimed is:

1. A method for aspirating and expelling fluid to and from a syringe comprising the steps of:
   providing an actuator having a cylinder-piston assembly and defining first and second chambers in said cylinder;
   admitting a measured quantity of pressurized hydraulic medium to said first chamber in said actuator;
   providing a syringe and coupling the motions of the piston of said syringe to the motions of the piston of said actuator;
   admitting a quantity of liquifiable gas to said second chamber of said actuator; whereby the saturated vapor pressure of said liquifiable gas exerts a counter-pressure on said piston in opposition to the pressure of said hydraulic medium.

2. A method as defined by claim 1, wherein said liquifiable gas is a substance selected from the group consisting of chlorine and fluorine derivatives of methane and ethane.

3. A method as defined by claim 2, wherein said gas has a saturated vapor pressure between 1.8 and 6 kg/cm$^2$ at 20° C.

4. A method as defined by claim 1, including the further step of transferring a measured quantity of hydraulic fluid under pressure from a calibrating chamber to said first chamber in said actuator.

5. A method as defined by claim 1, including the step of permitting the expansion of said liquifiable gas contained in said second chamber of said actuator and simultaneously aspirating fluid to said cylinder of said syringe.

6. An apparatus for aspirating and expelling fluid to and from a syringe, comprising:
   a syringe; including a piston moving within a cylinder;
   an actuator, including a piston moving within a cylinder and defining thereby a first chamber and a second chamber within said actuator;
   means for supplying a pressurized hydraulic medium to said first chamber of said actuator;
   means for admitting a quantity of liquifiable gas to said second chamber of said actuator;
   means for the preselection of the quantity of hydraulic medium admitted to said first chamber of said actuator; and
   flexible coupling means for providing fluid communication between said actuator and said means for preselection; said piston of said syringe being coupled to said piston of said actuator to share the motion thereof; whereby the pressure of the saturated vapor of said liquifiable gas exerts a counter-force on said piston of said actuator.

7. An apparatus as defined by claim 6, wherein said means for the preselection of the quantity of hydraulic medium includes a cylinder and a piston sliding in said cylinder, defining thereby two chambers the first of said chambers being directly connected to said means for supplying pressurized hydraulic medium and the second of said chamber serving for the preselection of the quantity of hydraulic medium, connected to said means for supplying pressurized medium by calibrating means and further comprising a main electromagnetic valve in series with a flow rate regulator connected between said preselection chamber and the output end of said means for preselecting the quantity of hydraulic medium and means for controlling the advance of said piston in said actuator by the controlled admission of pressurized hydraulic fluid.

8. An apparatus as defined by claim 7, wherein said calibrating means include a first inlet valve connected between the supply of hydraulic medium and the preselection chamber in said means for preselection and further comprising a first outlet valve connecting said preselection chamber to a reservoir open to atmospheric pressure.

9. An apparatus as defined by claim 7, wherein said means for controlling the slow advance of said actuator piston include a second inlet valve between said supply of hydraulic pressure and the output of said means for preselection and further comprising a second outlet valve connecting the output junction of said means for preselection with a reservoir open to atmospheric pressure.

10. An apparatus as defined by claim 6, wherein said actuator includes two parallel cylinder-piston assemblies, the piston rods of said assemblies being connected to move together, means for admitting pressurized fluid to said first chambers of said actuator and means for coupling the piston rod of said syringe to the piston rods of said actuator.

11. An apparatus as defined by claim 10, wherein said means for controlling the slow advance of said actuator pistons include a manual control valve coupled to the inlet of said actuator.

12. An apparatus as defined by claim 6, wherein said flexible coupling is made from electrically non-conducting material.

* * * * *